US008900197B2

(12) United States Patent
Crow

(10) Patent No.: US 8,900,197 B2
(45) Date of Patent: Dec. 2, 2014

(54) AUTOMATIC INJECTION MECHANISM WITH FRONTAL BUTTRESS

(75) Inventor: Doug Owen Crow, Brownsboro, TX (US)

(73) Assignee: West Pharmaceutical Services, Inc., Exton, PA (US)

( * ) Notice: Subject to any disclaimer, the term of this patent is extended or adjusted under 35 U.S.C. 154(b) by 406 days.

(21) Appl. No.: 12/530,539

(22) PCT Filed: Jun. 16, 2009

(86) PCT No.: PCT/US2009/047483
§ 371 (c)(1),
(2), (4) Date: Sep. 9, 2009

(87) PCT Pub. No.: WO2009/155277
PCT Pub. Date: Dec. 23, 2009

(65) Prior Publication Data
US 2011/0034879 A1 Feb. 10, 2011

Related U.S. Application Data

(60) Provisional application No. 61/074,253, filed on Jun. 20, 2008.

(51) Int. Cl.
*A61M 5/32* (2006.01)
*A61M 5/30* (2006.01)
*A61M 5/46* (2006.01)
*A61M 5/20* (2006.01)
*A61M 5/31* (2006.01)

(52) U.S. Cl.
CPC ............... *A61M 5/2033* (2013.01); *A61M 5/46* (2013.01); *A61M 2005/2073* (2013.01); *A61M 5/3204* (2013.01); *A61M 2005/3142* (2013.01); *A61M 5/3202* (2013.01); *A61M 2005/206* (2013.01)
USPC .......................... 604/197; 604/198; 604/135

(58) Field of Classification Search
CPC ........... A61M 5/2033; A61M 5/3202; A61M 5/3204; A61M 5/46; A61M 2005/206; A61M 2005/2026
USPC ................. 604/110, 187, 232, 234, 197–199, 604/135–136
See application file for complete search history.

(56) References Cited

U.S. PATENT DOCUMENTS 4,640,686 A 2/1987 Dalling et al.
5,451,210 A 9/1995 Kramer et al.
(Continued)

FOREIGN PATENT DOCUMENTS

CN 101072595 A 11/2007

OTHER PUBLICATIONS

Office Action Issued Apr. 18, 2011 in U.S. Appl. No. 12/749,836.
(Continued)

*Primary Examiner* — Quynh-Nhu H Vu
*Assistant Examiner* — Jenna Zhang
(74) *Attorney, Agent, or Firm* — Panitch Schwarze Belisario & Nadel LLP

(57) ABSTRACT

The present invention provides for an autoinjector that registers off a distal end of a syringe to provide for a more accurate needle insertion depth. The autoinjector employs an automatically deployable frontal buttress for registration of the distal end or shoulder of the syringe.

19 Claims, 8 Drawing Sheets

(56) References Cited

U.S. PATENT DOCUMENTS

| | | |
|---|---|---|
| 5,562,624 A | 10/1996 | Righi et al. |
| 5,843,036 A | 12/1998 | Olive et al. |
| 6,210,369 B1 | 4/2001 | Wilmot et al. |
| 6,387,078 B1 | 5/2002 | Gillespie, III |
| 6,428,528 B2 | 8/2002 | Sadowski et al. |
| 6,565,553 B2 | 5/2003 | Sadowski et al. |
| 6,986,760 B2 | 1/2006 | Giambattista et al. |
| 7,011,649 B2 | 3/2006 | De La Serna et al. |
| 7,066,907 B2 | 6/2006 | Crossman et al. |
| 7,297,136 B2 | 11/2007 | Wyrick |
| 7,314,464 B2 | 1/2008 | Giambattista et al. |
| 7,931,618 B2 | 4/2011 | Wyrick |
| 2004/0039336 A1 | 2/2004 | Amark et al. |
| 2004/0193110 A1 | 9/2004 | Giambattista et al. |
| 2005/0113750 A1 | 5/2005 | Targell |
| 2005/0283115 A1 | 12/2005 | Giambattista et al. |
| 2005/0288633 A1 | 12/2005 | Jeffrey |
| 2006/0270986 A1 | 11/2006 | Hommann et al. |
| 2007/0129686 A1 | 6/2007 | Daily et al. |
| 2007/0135767 A1* | 6/2007 | Gillespie et al. ............... 604/135 |
| 2007/0173770 A1* | 7/2007 | Stamp ........................... 604/187 |
| 2007/0265568 A1* | 11/2007 | Tsals et al. .................... 604/136 |
| 2007/0293819 A1 | 12/2007 | Giambattista et al. |
| 2008/0132838 A1 | 6/2008 | Wyrick |
| 2008/0228143 A1 | 9/2008 | Stamp |
| 2009/0005737 A1 | 1/2009 | Chun |
| 2009/0054849 A1 | 2/2009 | Burnell et al. |
| 2010/0152655 A1 | 6/2010 | Stamp |

OTHER PUBLICATIONS

Office Action issued Dec. 6, 2012 in CN Application No. 200980123335.X.

* cited by examiner

AUTOMATIC INJECTION MECHANISM WITH FRONTAL BUTTRESS

CROSS-REFERENCE TO RELATED APPLICATION

This application is a Section 371 of International Application No. PCT/US2009/047483, filed Jun. 16, 2009, which is not yet published, and this application claims the benefit of priority pursuant to 35 U.S.C. §119(e) of U.S. Provisional Patent Application No. 61/074,253, filed Jun. 20, 2008, the disclosure of which is hereby incorporated by reference in its entirety.

BACKGROUND OF THE INVENTION

The present invention relates to automatic injection devices ("autoinjectors"). In particular, the present invention relates to an autoinjector having an automatically deployable frontal buttress.

Autoinjector mechanisms have commercially been developed to substitute an automated mechanism for the manual action of inserting a hypodermic needle into a recipient's flesh and forcing the liquid medicament out of the syringe, through the hypodermic needle and into the recipient. In some cases, the automated mechanisms are designed to utilize commercially commonplace pre-filled syringes. The pre-filled syringes are typically manufactured by pharmaceutical companies, or in some cases a third party. The manufacturers thereafter assemble the pre-filled syringes into autoinjectors for commercial distribution. Examples of such devices include the EpiPen® manufactured by Meridian Medical Technologies, Inc., of Bristol, Tenn., the Humira® manufactured by Owen Mumford Ltd., of Oxford, United Kingdom, and the SureClick® system marketed by Scandinavian Health Limited, of Florham Park, N.J. Autoinjectors have proven to be beneficial for patients exhibiting psychological paranoia of receiving parenteral injections (e.g., needle phobic individuals and young children) and/or those without the manual dexterity or clear eyesight necessary to self-administer injections using conventional syringes.

Conventional autoinjectors generally provide a compression spring-based mechanism to drive the syringe in the distal direction within a housing (the housing contains the syringe) and some means to initiate the automatic injection process. When triggered, the compressed spring is released from end-to-end confinement. Typically, the spring is confined to abut against an interior surface of the housing about its proximal end such that releasing the compressed spring causes axial extension in the distal direction. The spring, typically acting through one or more surrogate components, impinges upon the syringe, and/or an elastomeric piston element thereof, causing the syringe to translate in the distal direction until the hypodermic needle associated with the syringe extends beyond the distal end of the housing.

The extended length of the needle determines the depth of drug delivery at the injection site. The exposed length of the needle (i.e., that portion of the needle exterior to the autoinjector housing at needle extension) is known as the "needle insertion depth." The correlation between extended length and insertion depth assumes that the distal end of the autoinjector is pressed against the injection site during autoinjector actuation. In most therapeutic applications, it is important that the depth of needle insertion be accurately controlled so as to assure the drug is delivered into a specific tissue mass, for example the subcutaneous tissue residing between the dermal skin layer and the musculature. Known and repeatable length of needle insertion is therefore a desirable attribute of autoinjector devices.

Billions of pre-filled syringes as described above are manufactured of borosilicate glass on an annual basis. The proximal end of the glass syringe is formed into a radially disposed, disk-shaped flange. The flange is thereafter cut on two sides in parallel planes in close proximity to the syringe body to form oblong and opposing finger grips. This glass syringe configuration is know as a cut-flange configuration. Glass syringes, and more particularly cut flange syringes, represent a number of challenges in autoinjector applications because they are fragile and easily broken components with a relatively high degree of dimensional variability. The high degree of dimensional variability leads to variability in the exposed length of the hypodermic needle beyond the distal end of the glass syringe and the overall length of the syringe. In addition, the cut flanges of such glass syringes have varying degrees of irregularity and asymmetry with respect to a central axis along the center of the syringe barrel and a plane perpendicular to the central axis.

Conventional autoinjectors are configured to stop the syringe at a desired forward position at the end of needle insertion based off of the syringe flange. That is, the syringe flange becomes a de facto point of registration, in other words a datum surface, which dictates the relative axial relationship between the syringe features and the other elements of the autoinjector. Under such configurations, any variability, whether associated with the overall length of the syringe, length of the exposed needle, or variability associated with the flange itself, translates directly into variability in the extended needle length and needle insertion length. In addition, due to the abrupt deceleration of the syringe/carrier assembly at the end of needle insertion, impact loads are imposed on the fragile syringe flanges. In other words, the force applied by the autoinjector in driving the syringe distally creates an opposing force imposed on the flange by its registration point of contact. In addition, a bending moment is borne by the flange as a result of the radial distance between the centerline of the piston and the flange. The bending moment increases the stress applied to the fragile flange increasing the risk of fracture.

Moreover, conventional autoinjectors are typically configured with a fixed stroke length. That is, conventional autoinjectors are designed to drive the plunger of the syringe a fixed distance from some fixed reference point on the autoinjector. Thus, with increased variability in the overall length of the glass syringe used in such autoinjectors, the fixed stroke length results in increased variability of residual medicament volume after injection. Such variability in residual medicament volume translates into significant monetary waste due to the relatively high cost of the drugs used to manufacture the medicaments.

Thus, conventional autoinjectors are deficient in that they cannot accommodate conventional pre-filled glass syringes (i.e., staked-needed syringes) to effectively address the issues associated with fragile and irregular components while assuring accurate needle placement and precise dose delivery due to the dimensional variability of glass syringe manufacturing. As such, there is still a need for an autoinjector that can provide accurate needle insertion depth and precise dose delivery.

In addition, conventional pre-filled glass syringes are typically supplied as an assembly with a needle shield that includes an elastomeric element to provide a means to sealably encapsulate the hypodermic needle. FIG. 2A illustrates a conventional pre-filled glass syringe 46 having a barrel 51.

The needle shield 60 serves as a sterility barrier for the needle 61 (FIG. 2B) and its fluid contents as the syringe 46 is pre-sterilized at the factory. Once delivered to the pharmaceutical company, the pre-filled syringe is filled with medicament within a sterile filling suite. Often, the needle shield 60 is itself encapsulated with a rigid component to provide additional protection against needle damage and to provide a suitable means to manually remove the needle shield 60. Thus, the needle shield 60 is commonly know as a rigid needle shield ("RNS"). In such RNSs, an open end allows access to the elastomeric interior through which the needle 61 is introduced into the elastomeric interior. The RNS is removably attached to the syringe 46 by a circumferential compression fit between the compliant elastomeric element of the RNS and cooperative features present on the distal end of the syringe 46. In addition, such RNSs have an overall outer diameter that is approximately the same as that of the syringe 46.

Such conventional syringes 46 can be used as a stand alone manually operable syringe 46 or in combination with a suitable autoinjector. Such autoinjectors are provided with a means to remove the RNS before administering the injection. This is typically accomplished by a component provided as part of the autoinjector that engages the needle shield during final assembly and provides a graspable handle with which a user can grasp to extract the needle shield in the axial, distal direction. However, the use of such handles to disengage the RNS creates an annular void or open end about the distal end of the autoinjector. Moreover, as the handle to remove the RNS occupies space at the distal end on the autoinjector, this precludes the use of such space for any potential buttress surface upon which the syringe 46 may engage.

Consequently, an autoinjector that is capable of accommodating a glass, cut flange syringe with a RNS attached would present pharmaceutical companies with a significant advantage in being able to provide one primary pre-filled syringe that can be used either in a manual setting or, alternatively, in conjunction with an autoinjector.

BRIEF SUMMARY OF THE INVENTION

In accordance with the present invention, the problems associated with variability and reliability of the needle insertion depth of autoinjectors employing the use of conventional pre-filled glass syringes are solved by registering the stop of the syringe within an autoinjector based upon the front end of the syringe.

In a preferred embodiment, the present invention comprises an autoinjector. The autoinjector includes a housing and a frontal buttress connected to a distal end of the housing. A syringe is housed within the housing and includes a barrel having a shoulder about a distal end of the barrel. An injection assembly is operatively connected to the syringe and configured to bias the syringe from an initial position in which the syringe is shrouded by the housing to an extended position in which a portion of the syringe extends beyond the housing. The frontal buttress is configured to move from a first, open position when the syringe is in the initial position to a second, closed position to engage the shoulder of the syringe when the syringe is in the extended position.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
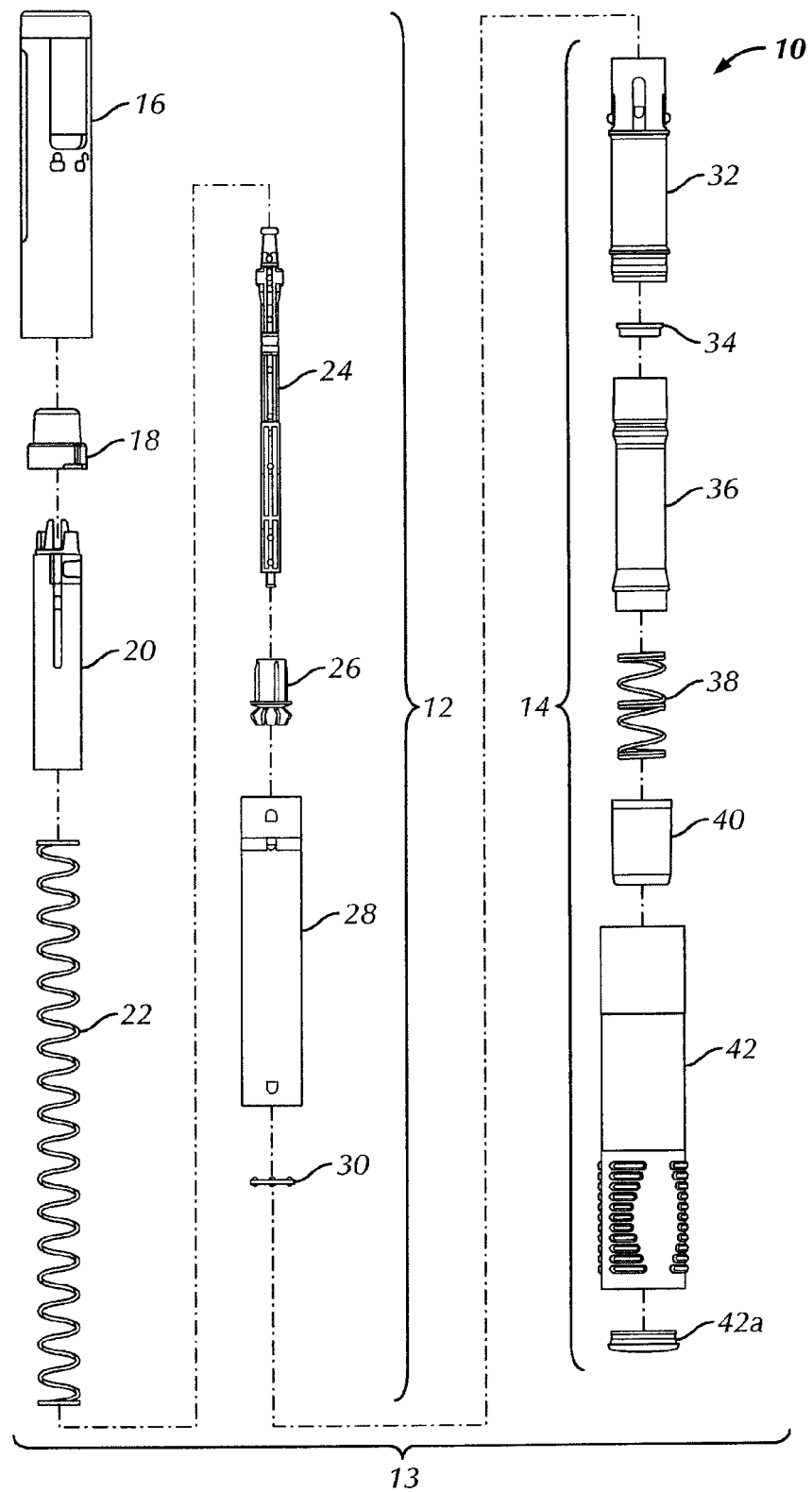
FIG. 1 is an exploded elevational view of the window tube subassembly and injection assembly of an autoinjector in accordance with a preferred embodiment of the present invention.

In a preferred embodiment, the present invention provides for an automatic injection device that includes an automatically deployable buttress upon which a syringe can be registered. As shown in FIGS. 1, 3, 6 and 7, the autoinjector 10 includes a housing 13 generally formed by various components of an injection assembly (or power pack subassembly) 12 and a window tube subassembly 14, such as an inner housing 20, a mid housing 28, a window tube 32 and a nose 40. While the present embodiment preferably includes an injection assembly 12, it is within the intent and scope of the present invention, that any injection assembly capable of automatically deploying or of causing a syringe to be automatically injected, can be used. For example, exemplary automatic injection devices applicable to the present invention include those disclosed in U.S. Pat. No. 6,387,078 to Gillespie, III, the disclosure of which is hereby incorporated by reference in its entirety. In general, the autoinjector 10 is configured to be a modular autoinjector 10 in which the injection assembly 12 and window tube subassembly 14 can be readily assembled with a conventional syringe 46 at the time of use. Such conventional syringes can also include plastic syringes and cartridge based syringes.

Figure 3:
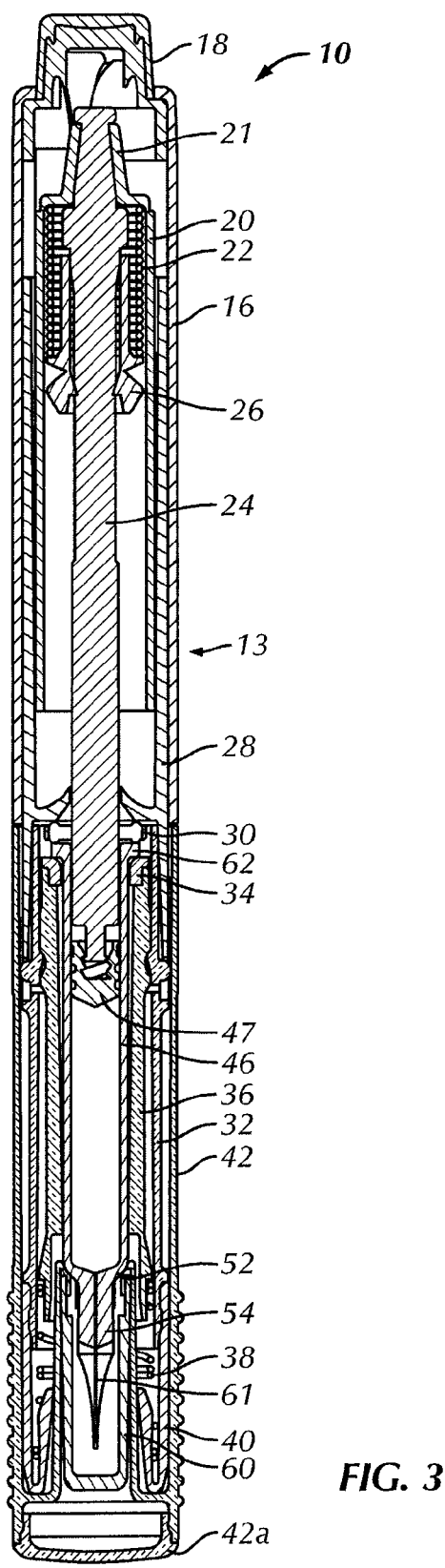
FIG. 3 is a cross-sectional elevational view of an autoinjector in accordance with a preferred embodiment of the present invention in a fully assembled state.
Figures 6, 7:
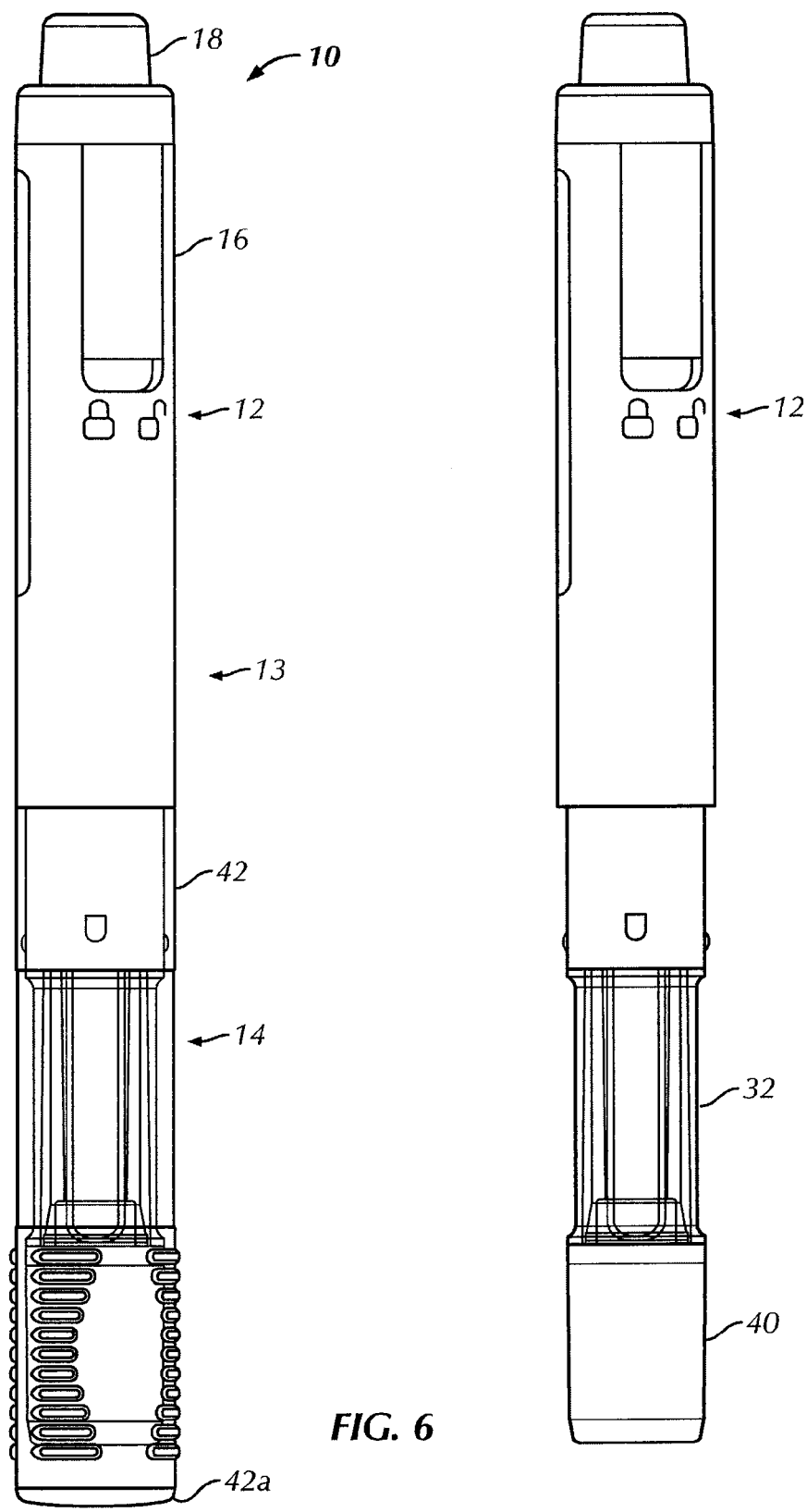
FIG. 6 is a side elevational view of the autoinjector of FIG. 3.
FIG. 7 is a side elevational view of the autoinjector of FIG. 6 with the handle removed.
Figure 8:
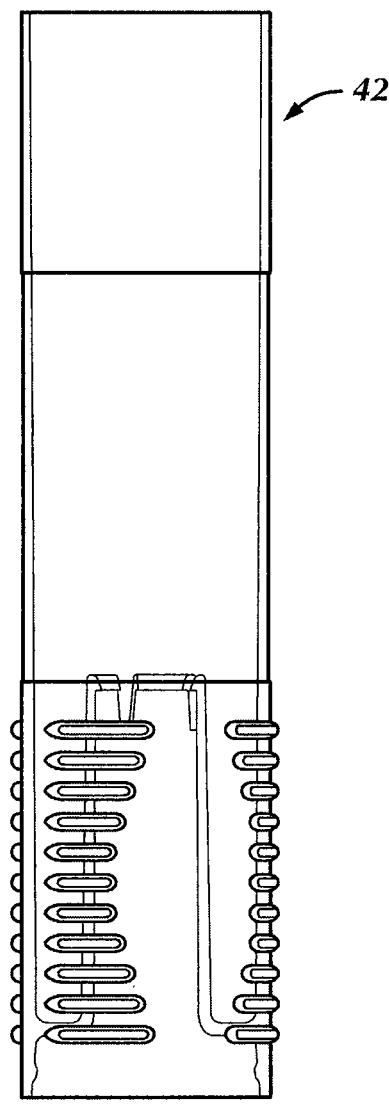
FIG. 8 is an enlarged side elevational view of the handle of FIG. 6.
Figure 9:
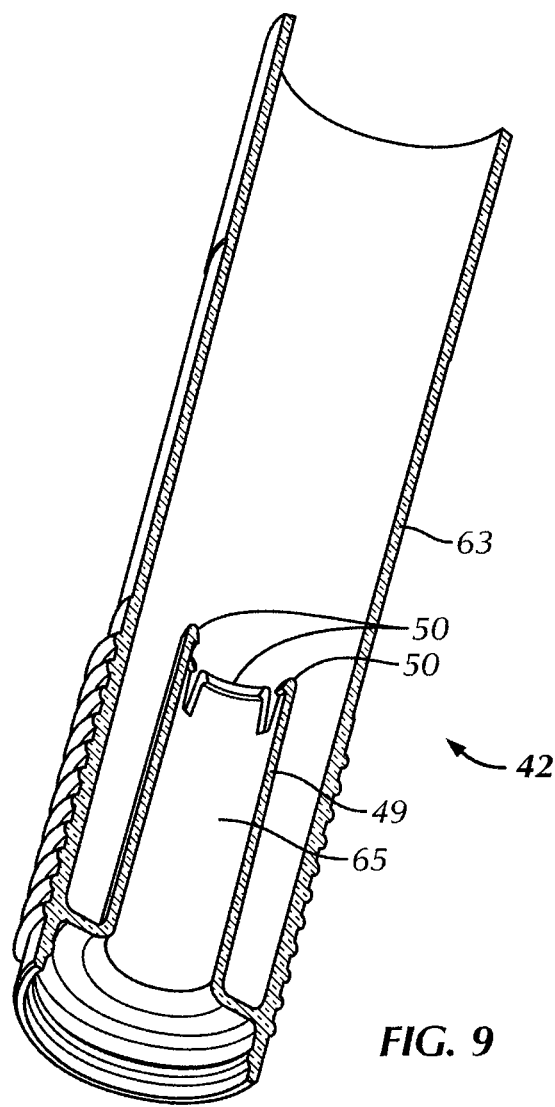
FIG. 9 is a cross-sectional perspective view of the handle of FIG. 8.
Figure 10:
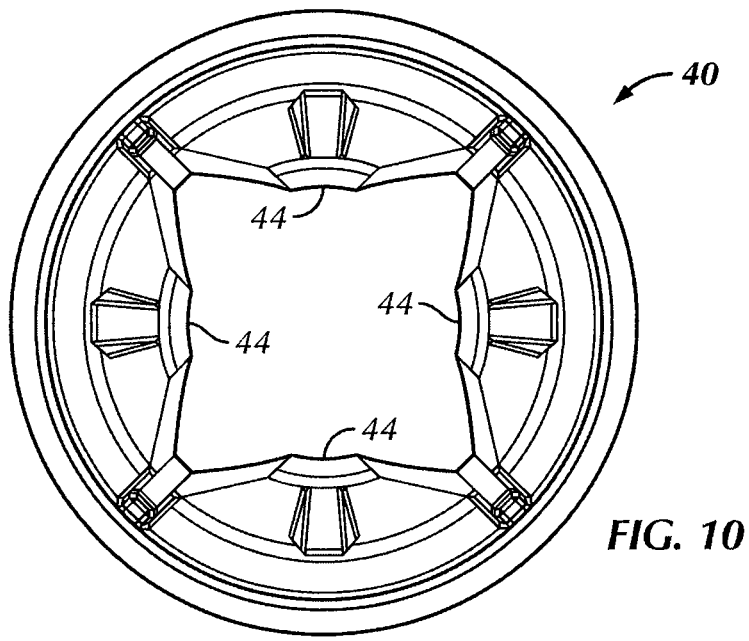
FIG. 10 is a top plan view of a nose of the autoinjector of FIG. 3.

Preferably the injection assembly 12 includes a cap 16, an activation button 18, an inner housing 20, an injection spring 22, a plunger rod 24 having a piston 47, a spring rest 26, a mid housing 28 and an optional syringe ring 30, as best shown in FIGS. 1 and 3. FIGS. 3 and 6 illustrate the injection assembly 12 in an assembled ready-to-use state and assembled to the window tube subassembly 14. As described hereinafter, distal refers to toward the needle-end of the autoinjector 10 and proximal refers to toward the button-end of the autoinjector 10.

In an assembled state, the spring rest 26 is releasably connected to about the middle of the plunger rod 24 by cooperating detents. The plunger rod 24 and spring rest 26 are positioned within the inner housing 20 with the injection spring 22 in between and proximal to the inner surface of the inner housing 20 and an outer surface of the spring rest 26. The injection spring 22 is maintained in a compressed state by catches 21 on the inner housing 20 that retain the proximal head of the plunger rod 24. The activation button 18 is positioned on top of the proximal end of the inner housing 20 and the cap 16 and functions to release the catches 21 to release the spring 22 upon depression. The foregoing assembly resides within the mid housing 28 and cap 16.

Figure 2A:
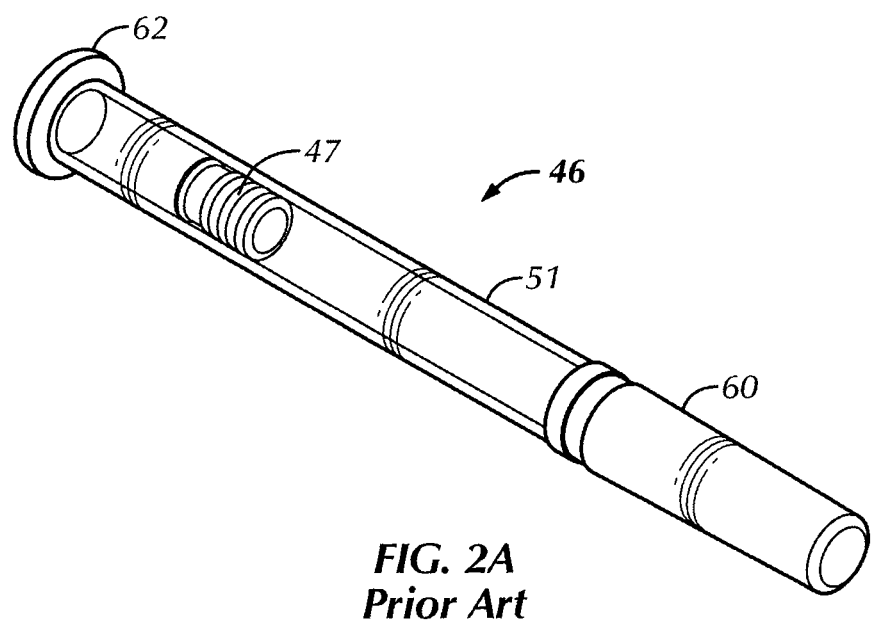
FIG. 2A is a perspective view of a conventional glass syringe with a rigid needle shield applicable for use within the autoinjector of FIG. 1.

Referring back to FIG. 1, the window tube subassembly 14 includes a window tube 32, a syringe cushion 34, a syringe guide 36, a return spring 38, a nose 40, a handle 42 and a handle cap 42a. FIG. 3 illustrates the syringe 46 housed within the housing 13. The syringe 46 includes a barrel 51 and a shoulder 52 about a distal end of the barrel 51 (FIG. 2A). FIGS. 3 and 6 illustrate the window tube subassembly 14 in an assembled ready-to use state and assembled with the injection assembly 12.

The syringe guide 36 is housed within the housing 13, is generally cylindrical in shape, and is configured to receive the barrel 51 of a syringe 46. When assembled with the syringe 46, the flange 62 of the syringe 46 rests upon the cushion 34 and the proximal end of the syringe guide 36 (see FIG. 3) and the nose 54 of the syringe 46 extends partially beyond the distal end of the syringe guide 36 (see FIGS. 3 and 4A). As a result, the syringe 46 moves in tandem with the syringe guide 36 upon the distal movement of the syringe guide 36.

Figure 4A:
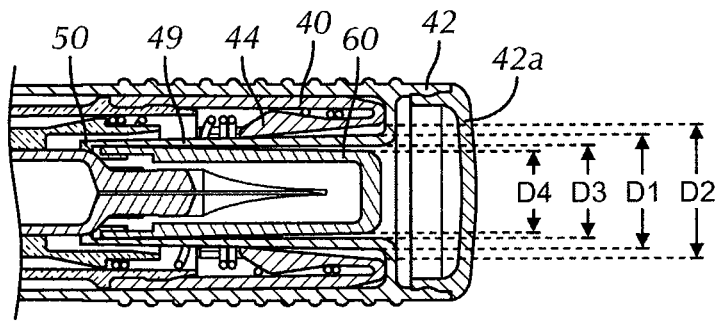
FIG. 4A is an enlarged cross-sectional elevational view of the distal end of the autoinjector of FIG. 3 with a handle in a fully assembled position.

The handle 42 (as shown in FIGS. 1, 3, 4A-C, 6, 8 and 9) is releasably connected to the distal end of the housing 13. The handle 42 includes a body 63 that is generally cylindrical in shape and configured to receive the assembly of the window tube 32, syringe cushion 34, syringe 46, syringe guide 36, return spring 38 and nose 40. The distal end of the handle 42 is also configured with a needle shield remover 49 (FIG. 9) having a generally cylindrical body 65 and latches 50 at the most proximal end of the needle shield remover 49. The needle shield remover 49 is integrally formed and connected to the distal end of the handle 42. Alternatively, the needle shield remover 49 can be a separate component secured to the handle 42. The needle shield remover 49 is configured to be received within the nose 40 and over the needle shield 60. That is, the needle shield remover 49 is sized with an outside diameter (D1) that is at least slightly smaller than the inside diameter (D2) of the flexible members 44 when in the fully opened position and an inside diameter (D3) that is at least slightly greater than the outside diameter (D4) of the needle shield 60, as best shown in FIG. 4A. Thus, the needle shield remover 49 is configured to maintain the plurality of radially disposed circumferentially spaced flexible members 44 in the first position (i.e., open position), as shown in FIG. 4A.

The latches 50 (FIG. 9) can be configured as a radially inwardly disposed flange which engages the proximal end of the needle shield 60. As a result, when the handle 42 is removed, the latches 50 engage the needle shield 60 to thereby also remove the needle shield 60 from the syringe 46. In addition, the latches 50 are preferably configured with a chamfered proximal surface to provide ease of assembly over the needle shield 60.

Figure 2B:
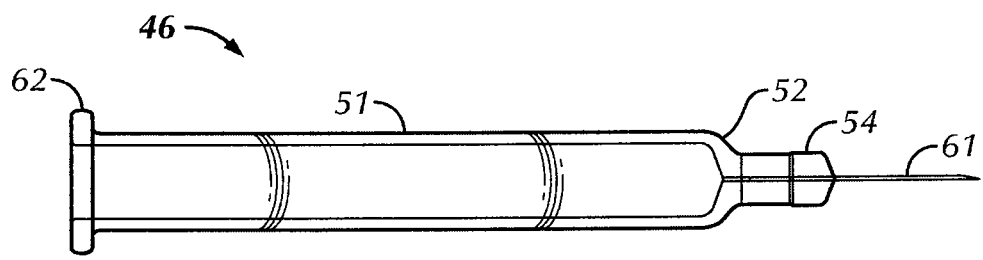
FIG. 2B is a side partial cross-sectional view of the syringe of FIG. 2A without the rigid needle shield.
Figure 5A:
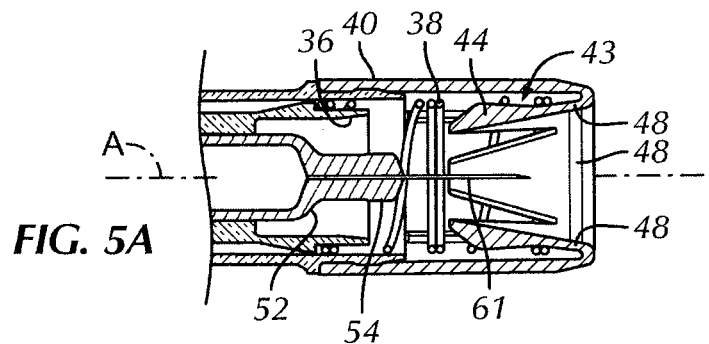
FIG. 5A is an enlarged cross-sectional elevational view of the distal end of the autoinjector of FIG. 3 with the handle completely removed and in a pre-activation state.
Figure 5B:
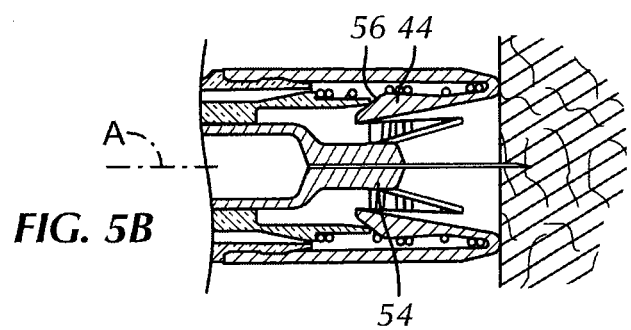
FIG. 5B is an enlarged cross-sectional elevational view of the distal end of the autoinjector of FIG. 3 with a syringe guide initially engaging flexible members of a frontal buttress.
Figure 5C:
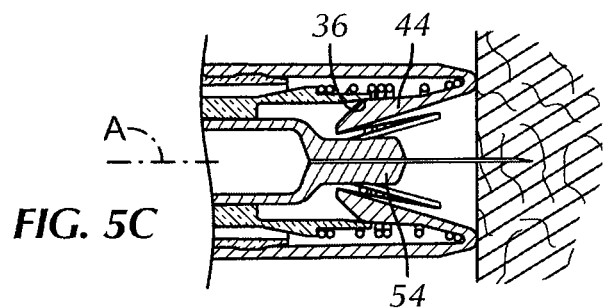
FIG. 5C is an enlarged cross-sectional elevational view of the distal end of the autoinjector of FIG. 3 with the syringe guide engaging an outer surface of the flexible members of the frontal buttress.
Figure 5D:
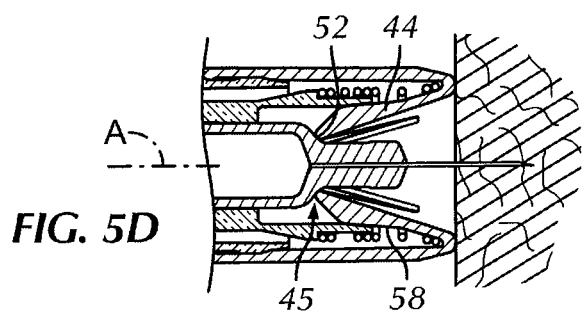
FIG. 5D is an enlarged cross-sectional view of the distal end of the autoinjector of FIG. 3 with a shoulder of the syringe engaging a buttress surface formed by the frontal buttress.

In an assembled state, as shown in FIG. 3, the handle cap 42a is secured to the handle 42 and the nose 40 is assembled to the window tube 32. The return spring 38 seats within the nose 40 and the syringe guide 36 resides on top of the return spring 38 with the syringe cushion 34 residing on the syringe guide 36. The return spring 38, syringe guide 36 and syringe cushion 34 reside within the window tube 32, which mates with the nose 40. A syringe 46 (e.g., a pre-filled glass syringe, as shown in FIGS. 2A and 2B) is inserted into the syringe guide 36 such that the syringe ring 30 rests upon a proximal edge of the flange 62 of the syringe 46 and the plunger rod 24 is inserted within the barrel of the syringe 46. The syringe 46 is maintained in radial confinement within the syringe guide 36 by a running annular fit between the exterior of the syringe 46 and the interior bore of the syringe guide 36. The syringe 46 is maintained in axial relation to the syringe guide 36 by force applied to the proximal end of the syringe 46 by the injection spring 22 acting upon the syringe 46 through one or more components. As such, the syringe 46 and syringe guide 36 travel in tandem upon activation until the syringe 46 engages a buttress surface 45 formed by a frontal buttress 43, as shown in FIG. 5D.

To activate the injection assembly 12, a user removes the handle 42, and presses the nose 40 against the injection site and depresses activation button 18, thereby causing the plunger rod 24 to disengage from the inner housing 20. Upon disengagement of the plunger rod 24, the injection spring 22, which is initially in the compressed state, expands to exert a driving force on the spring rest 26 that is connected to the plunger rod 24, which subsequently causes the syringe 46 to move distally. In sum, the injection assembly 12 is operatively connected to the syringe 46 and configured to bias the syringe 46 from an initial position (FIG. 4A) in which the syringe 46 is shrouded by the housing 13 to an extended position (FIG. 5D) in which a portion of the syringe 46 extends beyond the housing 13.

FIGS. 5A-D, 9 and 10 illustrate a frontal buttress 43 connected to a distal end of the housing 13. The frontal buttress 43 includes a plurality of radially disposed circumferentially spaced flexible members 44. The flexible members 44 are generally configured in a pyramidal-like shape such that when in the closed position (see FIG. 5D) the flexible members 44 form a generally frustroconical shape with the smaller diameter section proximal to the larger diameter section. Preferably, the radially disposed circumferentially spaced flexible members 44 are located on an interior of the housing 13 and extend proximally from the distal end of the housing 13 such that the flexible members 44 collectively form a buttress surface 45 that engages the shoulder 52 of the syringe 42.

Figure 11:
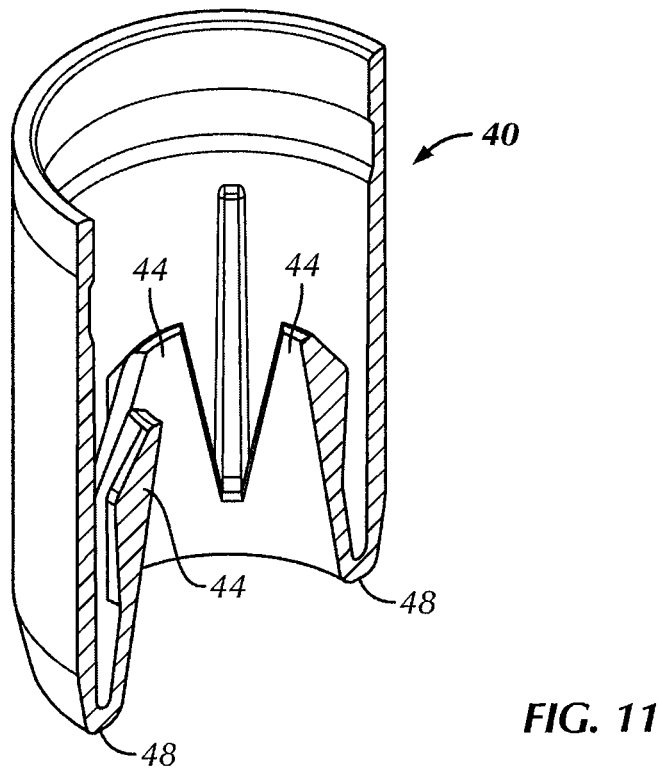
FIG. 11 is a cross-sectional perspective view of the nose of FIG. 10.

In the present embodiment, the nose 40 is configured to include the frontal buttress 43. The bases 48 of each of the flexible members 44 are connected to the nose 40 along the interior distal end of the nose 40, as best shown in FIGS. 5A and 11. The connection of the flexible members 44 to the nose 40 is configured as a flexible connection such that the flexible members 44 can flex between a first open or spread apart position/state (as shown in FIG. 4A) and a second closed, closer together position/state (as shown in FIG. 5D). The flexible members 44 are also configured to be biased toward the closed position. The biasing force results from the flexible members 44 initially being molded and configured to be in the closed position and then being forced into the open position by the handle 42. As a result, due to the tensile properties of the frontal buttress 43, the flexible members 44 maintain a radially inward bias. That is, the flexible members 44 flex radially inwardly when in the closed state.

In sum, the frontal buttress 43 is configured to move from a first open position (FIG. 4A) when the syringe 46 is in the initial position to a second closed position (FIG. 5D) to engage the shoulder 52 of the syringe 46 when in the extended position. The flexible members 44 can be made from any polymer, such as a rigid plastic or thermoplastic elastomer. Preferably, the flexible members 44 are made from a polyacetal or a thermoplastic elastomer.

Figure 4B:
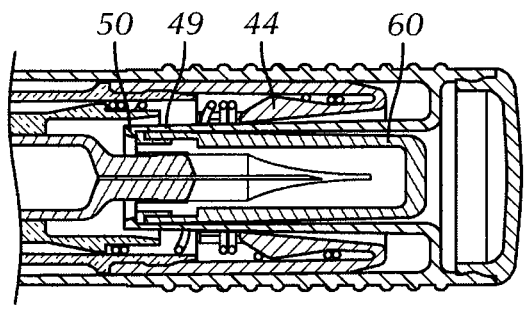
FIG. 4B is an enlarged cross-sectional elevational view of the distal end of the autoinjector of FIG. 3 with the handle in a partially removed position.
Figure 4C:
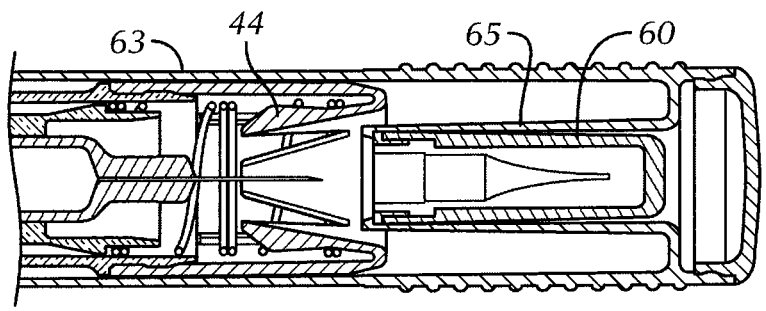
FIG. 4C is an enlarged cross-sectional elevational view of the distal end of the autoinjector of FIG. 3 with the handle in a further partially removed position.

As shown in FIGS. 4A-C, the nose 40 is assembled with the handle 42. In the fully assembled state, the handle 42 is fully inserted onto the nose 40 such that the shield remover 49 of the handle 42 forces the flexible members 44 into the open position (FIG. 4A). FIGS. 4B and 4C illustrate various stages of removal of the handle 42 from the autoinjector 10. As best shown in FIGS. 4B and 4C, as the handle 42 is removed, the latches 50 of the needle shield remover 49 simultaneously remove the needle shield 60. After the handle 42 is removed, the bias of the flexible members 44 causes the flexible members 44 to initially move toward a centerline (A), flexing at the base 48, thereby reorienting the proximal ends of the flexible members 44 to a position within the inside diameter of the syringe guide 36 (i.e., a pre-activation or ready-to-use state, as shown in FIG. 5A).

After the handle 42 is removed and upon activation of the autoinjector 10, the injection assembly 12 forces the syringe guide 36/syringe 46 assembly to engage the frontal buttress 43. As shown in FIGS. 5A-5D, as the syringe guide 36/syringe 46 assembly moves distally, a distal edge of the syringe guide 36 engage an outside surface of the flexible members 44. Preferably, the outside surface of the flexible member 44 includes a chamfered or inclined surface 56 that slopes radially inwardly. Upon continued distal movement of the syringe guide 36/syringe 46 assembly, the distal edge of the syringe guide 36 slidingly engages the flexible members 44 causing the flexible members 44 to collectively deflect inwardly toward the centerline (A) of the autoinjector (FIG. 5D). Preferably, the syringe guide 36/syringe 46 assembly is configured such that the nose 54 of the syringe 46 initiates passage through the nose 40 of the autoinjector 10 prior to the flexible members 44 completely flexing inwardly. Upon full deployment of the syringe 46, by the radial confinement and column strength of the flexible members 44, the proximal ends of the flexible members 44 advantageously provide for an effective buttress surface 45 to the shoulder 52 of the syringe 46. Moreover, at the end of needle insertion and once the syringe 46 abuts against the buttress surface 45 (as shown in FIG. 5D) the syringe 46 remains in contact with the buttress surface 45 while liquid medicament is forced out of the syringe 46 and into the injection site.

Preferably, the flexible members 44 are also configured with a planar outside surface 58 that is oriented substantially parallel to the centerline (A) when the flexible members 44 are in the closed position, as best shown in FIG. 5D. The substantially parallel outside surface 58 advantageously allows for sliding engagement (or play) between the flexible members 44 and the syringe guide 36, such that the syringe guide 36 can accommodate a wide range of variability in the overall length of the syringe 46 and still function to close the flexible members 44 without bottoming out at the base 48 of the frontal buttress 43. Moreover, the sliding relationship assures engagement of the frontal buttress 43 by the syringe 46 without risk of stressing the syringe flange 62.

In sum, the present invention advantageously provides for an autoinjector that can accommodate a conventional syringe (such as a pre-filled glass syringe) and provide a robust means to automatically stop forward (i.e., distal) movement and provide a more consistent and accurate frontal position during needle insertion (i.e., needle insertion depth) and dose delivery, respectively, by registering the stop of needle depth insertion upon the shoulder 52 of the syringe 46 rather than the flange 62. By eliminating the load on the syringe flange 62, the risk of syringe flange fracture is also significantly reduced. Moreover, the accuracy of dose delivery and reduction in residual fluid volume within the syringe post-injection is significantly enhanced, thus saving considerable costs associated with manufacturing pre-filled syringes. The present invention also advantageously provides for an autoinjector having an automatically deployable frontal buttress 43 such that the forward end of the syringe 46 becomes the load bearing or datum surface, thereby reducing stress on the syringe flange 62 and reducing variability in needle insertion depth by eliminating the variability associated with overall length and flange dimensions of glass syringes.

In addition, as the present invention is configured for use with conventional pre-filled syringes, such as glass staked-needle syringes, plastic syringes, and cartridge based syringes with needle hubs, there is no need for any additional sterilization of the autoinjector after assembly with the pre-filled syringe as the medicament within the pre-filled syringe is maintained within a sterile environment regardless of the sterility of the autoinjector. This helps reduce the overall costs associated with autoinjector manufacturing. In addition, because of the modular configuration of the present invention, it allows for pre-filled syringes to be assembled and prepared at one location and the autoinjector components to be prepared at a separate location and/or at different times, thus allowing for greater manufacturing versatility. Moreover, as the autoinjector of the present invention can be assembled with conventional pre-filled syringe at the time of use, the two devices are not constrained to a single expiration date of the device. Thus, the usability or shelf life of the autoinjector will not depend upon the expiration date of the pre-filled syringe.

It will be appreciated by those skilled in the art that changes could be made to the embodiment described above without departing from the broad inventive concept thereof. It is understood, therefore, that this invention is not limited to the particular embodiment disclosed, but is intended to cover modifications within the spirit and scope of the present invention as defined by the claims.

What is claimed is:

1. An autoinjector comprising:
  a housing;
  a frontal buttress comprises a plurality of radially disposed circumferentially spaced flexible members connected to a distal end of the housing;
  a syringe housed within the housing, the syringe including a barrel having a shoulder about a distal end of the barrel; and an injection assembly operatively connected to the syringe and configured to bias the syringe from an initial position in which the syringe is shrouded by the housing to an extended position in which a portion of the syringe extends beyond the housing, wherein each of the flexible members flexes from a first open position in which the flexible members are in an open state in which the plurality of flexible members are spaced from the shoulder of the barrel of the syringe when the syringe is in the initial position to a second closed position in which the plurality of flexible members are in a closed state abutting the shoulder of the barrel of the syringe when the syringe is in the extended position.

2. The autoinjector of claim 1, wherein at least a proximal end of each of the flexible members flexes radially inwardly when in the closed state.

3. The autoinjector of claim 1, wherein the radially disposed circumferentially spaced flexible members are located on an interior of the housing and extend proximally from the distal end of the housing such that the flexible members collectively form a buttress surface that abuts the shoulder of the syringe.

4. The autoinjector of claim 1, further comprising a syringe guide within the housing, wherein the syringe is located within the syringe guide and moves in tandem with the syringe guide upon the distal movement of the syringe guide and wherein a distal edge of the syringe guide engages and moves each of the radially disposed circumferentially spaced flexible members inwardly.

5. The autoinjector of claim 1, further comprising a handle releasably connected to the distal end of the housing, the handle including:
a cylindrical body; and
a needle shield remover connected to the cylindrical body and configured to remove a needle shield.

6. The autoinjector of claim 5, wherein the needle shield remover comprises:
a generally cylindrical body; and
a latch for engaging a proximal end of the needle shield.

7. The autoinjector of claim 5, wherein the needle shield remover is configured to maintain the plurality of radially disposed circumferentially spaced flexible members in the first position.

8. The autoinjector of claim 1, wherein the syringe is a staked-needle syringe.

9. The autoinjector of claim 1, wherein the syringe is a pre-filled syringe.

10. An autoinjector comprising:
a housing having a distal end;
a syringe supporting a needle, the syringe having a shoulder proximate the needle;
a needle shield for covering the needle;
a drive mechanism to move the syringe between a first position wherein the needle is retracted within the housing and a second position wherein the needle is extended outside the housing; and
a buttress member having a plurality of flexible members, each flexible member movable between a first radial orientation and a second radial orientation; and
wherein with the syringe in the first position and the flexible members in the first radial orientation, at least a portion of the needle shield fits within the flexible members and the flexible members are spaced from the shoulder and with the syringe in the second position and the flexible members in the second radial orientation, the flexible members abut the shoulder.

11. The autoinjector of claim 10, further comprising a syringe guide that moves with the syringe as the syringe moves from the first position to the second position, wherein the syringe guide engages the flexible members to move the flexible members at least a portion of the way from the first radial orientation to the second radial orientation.

12. The autoinjector of claim 10, wherein the flexible members each have a first end attached to a supporting structure and a second end pivotable about the first end.

13. The autoinjector of claim 12, wherein the second end pivots radially inwardly as the flexible member moves from the first radial orientation to the second radial orientation.

14. The autoinjector of claim 12, wherein the second end of each flexible member is attached to the housing.

15. The autoinjector of claim 10, further comprising a cap including a needle shield removal element directly engaged with the needle shield.

16. The autoinjector of claim 15, wherein the flexible members are biased into the first radial orientation by engagement of the flexible members with the needle shield removal element.

17. The autoinjector of claim 16, wherein, with the needle shield directly engaged with the needle shield removal element, removal of the cap from the housing also removes the needle shield from the needle.

18. The autoinjector of claim 17, wherein upon removal of the cap and needle shield, the flexible members move from the first radial orientation toward the second radial orientation due to elasticity of the flexible members.

19. The autoinjector of claim 15, wherein the needle shield removal element is formed integrally with the cap member.

* * * * *